United States Patent
Amit et al.

(10) Patent No.: US 8,626,275 B1
(45) Date of Patent: Jan. 7, 2014

(54) APPARATUS AND METHOD FOR DETECTING MYOCARDIAL ISCHEMIA USING ANALYSIS OF HIGH FREQUENCY COMPONENTS OF AN ELECTROCARDIOGRAM

(75) Inventors: Guy Amit, Ganei-Tikva (IL); Oded Luria, Tel-Aviv (IL); Eran Toledo, Tel Aviv (IL); Yair Granot, Modiln (IL); Tamir Ben-David, Tel-Aviv (IL)

(73) Assignee: BSP Biological Signal Processing Ltd., Tel-Aviv (IL)

( * ) Notice: Subject to any disclaimer, the term of this patent is extended or adjusted under 35 U.S.C. 154(b) by 0 days.

(21) Appl. No.: 13/552,712

(22) Filed: Jul. 19, 2012

Related U.S. Application Data

(60) Provisional application No. 61/667,482, filed on Jul. 3, 2012.

(51) Int. Cl.
*A61B 5/0402* (2006.01)

(52) U.S. Cl.
USPC ........................................................ 600/509

(58) Field of Classification Search
USPC .......................... 600/508–509, 515–516, 523
See application file for complete search history.

(56) References Cited

U.S. PATENT DOCUMENTS

| | | |
|---|---|---|
| 4,422,459 A | 12/1983 | Simson |
| 5,046,504 A | 9/1991 | Albert et al. |
| 5,117,833 A | 6/1992 | Albert et al. |
| 5,348,020 A | 9/1994 | Hutson |
| 5,404,877 A | 4/1995 | Nolan et al. |
| 5,655,540 A | 8/1997 | Seegobin et al. |
| 5,954,664 A | 9/1999 | Seegobin |
| 6,128,526 A | 10/2000 | Stadler et al. |
| 6,600,949 B1 | 7/2003 | Turcott |
| 7,113,820 B2 | 9/2006 | Schlegel et al. |
| 7,151,957 B2 | 12/2006 | Beker et al. |
| 7,239,988 B2 | 7/2007 | Hasson et al. |
| 7,386,340 B2 | 6/2008 | Schlegel et al. |
| 7,412,283 B2 | 8/2008 | Ginzburg et al. |
| 7,539,535 B1 | 5/2009 | Schlegel et al. |
| 2003/0013978 A1 | 1/2003 | Schlegel et al. |
| 2003/0208129 A1 | 11/2003 | Beker et al. |
| 2004/0039292 A1* | 2/2004 | Schlegel et al. ............... 600/509 |
| 2005/0177049 A1 | 8/2005 | Hardahl et al. |
| 2006/0074451 A1 | 4/2006 | Chen et al. |
| 2007/0066907 A1 | 3/2007 | Beker et al. |

(Continued)

FOREIGN PATENT DOCUMENTS

| | | |
|---|---|---|
| WO | WO 2005/104937 | 11/2005 |
| WO | WO 2008/015683 | 2/2008 |

OTHER PUBLICATIONS

International Search Report and the Written Oponion Dated Jul. 18, 2008 From the International Searching Authority Re.: Application No. PCT/IL07/00971.

(Continued)

*Primary Examiner* — Rex R Holmes

(57) ABSTRACT

ECG apparatus comprises an ECG input for obtaining ECG signals; a high frequency analyzer configured for obtaining high frequency QRS components from a QRS complex within said ECG signals and identifying therein at least one reduced amplitude zone—RAZ—present within a given QRS complex; and a RAZ quantifier configured for obtaining a quantification of said at least one RAZ region within said QRS complex.

21 Claims, 8 Drawing Sheets
(7 of 8 Drawing Sheet(s) Filed in Color)

(56) References Cited

U.S. PATENT DOCUMENTS

| | | | |
|---|---|---|---|
| 2008/0188762 | A1 | 8/2008 | John et al. |
| 2008/0194978 | A1 | 8/2008 | Beker et al. |
| 2009/0318820 | A1 | 12/2009 | Toledo et al. |
| 2010/0222688 | A1 | 9/2010 | Fischell et al. |
| 2011/0152661 | A1 | 6/2011 | Feldman et al. |

OTHER PUBLICATIONS

Communication Pursuant to Article 94(3) EPC Dated Jul. 11, 2012 From the European Patent Office Re. Application No. 07790026.4.
Communication Pursuant to Rules 70(2) and 70a(2) EPC Dated Oct. 24, 2011 From the European Patent Office Re. Application No. 07790026.4.
International Search Report and the Written Opinion Dated Jul. 18, 2008 From the International Searching Authority Re. Application No. PCT/IL07/00971.
Office Action Dated Apr. 14, 2010 From the State Intellectual Property Office of the People's Republic of China Re. Application No. 200780035563.2 and Its Translation Into English.
Official Action Dated Mar. 6, 2013 From the US Patent and Trademark Office Re. U.S. Appl. No. 12/375,544.
Official Action Dated Jun. 10, 2011 From the US Patent and Trademark Office Re. U.S. Appl. No. 12/375,544.
Official Action Dated Feb. 27, 2012 From the US Patent and Trademark Office Re. U.S. Appl. No. 12/375,544.
Response Dated Dec. 6, 2011 to Official Action of Jun. 10, 2011 From the US Patent and Trademark Office Re. U.S. Appl. No. 12/375,544.
Response Dated Aug. 19, 2010 to Office Action of Apr. 14, 2010 From the State Intellectual Property Office of the People's Republic of China Re. Application No. 200780035563.2.
Response Dated Dec. 19, 2011 to Office Action of Oct. 19, 2011 From the State Intellectual Property Office of the People's Republic of China Re. Application No. 200780035563.2.
Supplementary European Search Report and the European Search Opinion Dated Oct. 5, 2011 From the European Patent Office Re. Application No. 07790026.4.
Translation of Office Action Dated Jul. 3, 2012 From the State Intellectual Property Office of the People's Republic of China Re. Application No. 200780035563.2.
Translation of Office Action Dated Oct. 19, 2011 From the State Intellectual Property Office of the People's Republic of China Re. Application No. 200780035563.2.
Abboud et al. "Analysis of High-Frequency Mid-QRS Potentials Vs ST Segment and T Wave Analysis for the Diagnosis of Ischemic Heart Disease", Computers in Cardiology, 30: 813-814, 2003.
Beker et al. "Analysis of High Frequency QRS Potential During Exercise Testing in Patients With Coronary Artery Disease and in Health Subjects", PACE, 19(Pt.I): 2040-2050, Dec. 1996.
Pettersson et al. "Changes in High-Frequency QRS Components are More Sensitive Than ST-Segment Deviation for Detecting Acute Coronary Artery Occlusion", Journal of the American College of Cardiology, JACC, 36(6): 1827-1834, 2000.
Rahman et al. "High-Frequency QRS Electrocardiogram Predicts Perfusion Defects During Myocardial Perfusion Imaging", Journal of Electrocardiology, 39: 73-81, 2006.
Sharir et al. "Detection of Stress-Induced Myocardial Ischemia Using Analysis of Depolarization Abnormalities", JACC, Abstracts—Imaging and Diagnostic Testing, A297: #1054-264, Mar. 10, 2009.
Sharir et al. "Incremental Diagnostic Value of High-Frequency QRS Analysis for Identifying Stress-Induced Ischemia", JACC, Exercise Testing: Modern Diagnostic and Prognostic Markers, Abstracts—Diagnostic Testing, 132A: #828-3, Mar. 13, 2006.

\* cited by examiner

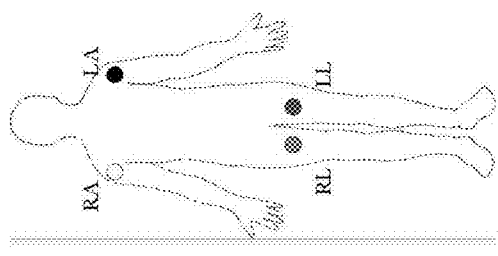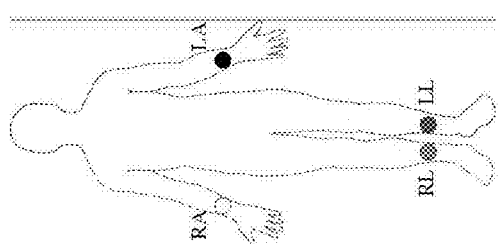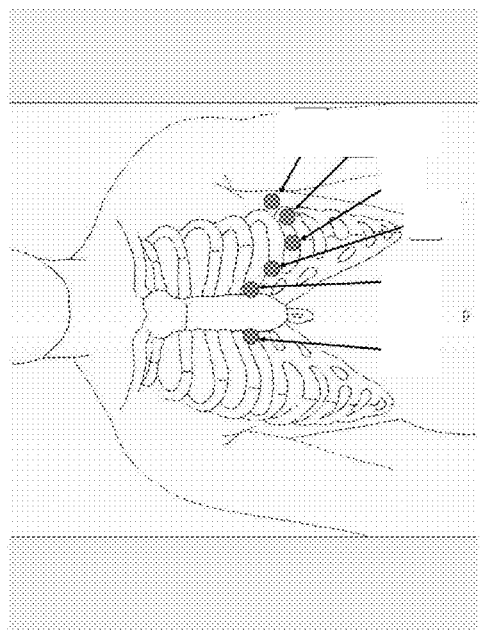
FIG. 2

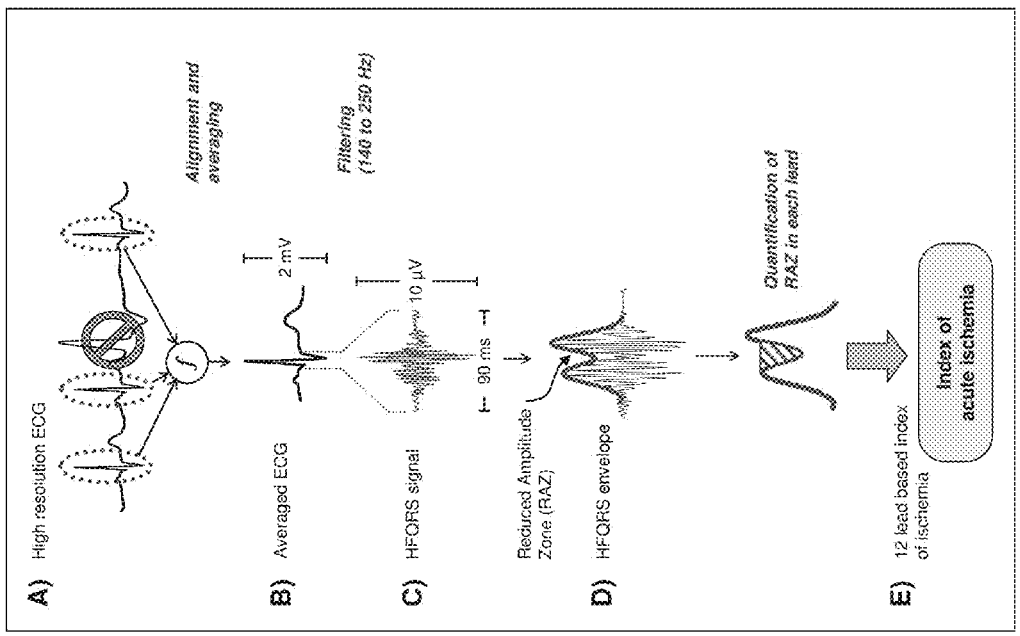

APPARATUS AND METHOD FOR DETECTING MYOCARDIAL ISCHEMIA USING ANALYSIS OF HIGH FREQUENCY COMPONENTS OF AN ELECTROCARDIOGRAM

RELATED APPLICATION

This application claims the benefit of priority under 35 USC §119(e) of U.S. Provisional Patent Application No. 61/667,482 filed Jul. 3, 2012, the contents of which are incorporated herein by reference in their entirety.

FIELD AND BACKGROUND OF THE INVENTION

The present invention, in some embodiments thereof, relates to an apparatus and method for detecting myocardial ischemia using analysis of high frequency components of an electrocardiogram, and more particularly but not exclusively to use of regions within the QRS complex known as reduced amplitude zones or RAZ.

ECG is used to measure the rate and regularity of heartbeats, as well as the size and position of the chambers, the presence of any damage to the heart, and the effects of drugs or devices used to regulate the heart.

ECG may be measured during rest (resting ECG) or when the heart is under stress (stress ECG).

Usually more than two electrodes are used, and they can be combined into a number of pairs (For example: left arm (LA), right arm (RA) and left leg (LL) electrodes form the three pairs LA+RA, LA+LL, and RA+LL). The output from each pair is known as a lead. Each lead looks at the heart from a different angle. Different types of ECGs can be referred to by the number of leads that are recorded, for example 3-lead, 5-lead or 12-lead ECGs. A 12-lead ECG is one in which 12 different electrical signals are recorded at approximately the same time and will often be used as a one-off recording of an ECG, traditionally printed out as a paper copy. 3- and 5-lead ECGs tend to be monitored continuously and viewed only on the screen of an appropriate monitoring device, for example during an operation or whilst being transported in an ambulance.

An ECG is the best way to measure and diagnose abnormal rhythms of the heart, particularly abnormal rhythms caused by damage to the conductive tissue that carries electrical signals, or abnormal rhythms caused by electrolyte imbalances. In a myocardial infarction (MI), the ECG can identify if the heart muscle has been damaged in specific areas, though not all areas of the heart are covered. Acute coronary syndrome (ACS) refers to any group of symptoms attributed to obstruction of the coronary arteries.

The ECG device detects and amplifies the tiny electrical changes on the skin that are caused when the heart muscle depolarizes and subsequently repolarizes during each heartbeat. At rest, each heart muscle cell has a negative charge, which causes the membrane potential, across its cell membrane. Decreasing this negative charge towards zero, via the influx of the positive cations, $Na^+$ and $Ca^{++}$, is called depolarization, which activates the mechanisms in the cell that cause it to contract. During each heartbeat, a healthy heart will have an orderly progression as a wave of depolarisation, that is triggered by the cells in the sinoatrial node, spreads out through the atrium, then passes through the atrioventricular node and finally spreads all over the ventricles. The progression is detected as waveforms in the voltage between two electrodes placed either side of the heart and may be displayed as a wavy line either on a screen or on paper. This display indicates the overall rhythm of the heart and weaknesses in different parts of the heart muscle.

A typical ECG tracing of the cardiac cycle (heartbeat) consists of a P wave, a QRS complex, a T wave, and a U wave which is normally visible in 50 to 75% of ECGs. The baseline voltage of the electrocardiogram is known as the isoelectric line. Typically the isoelectric line is measured as the portion of the tracing following the T wave and preceding the next P wave.

The standard ECG traces ignore, indeed usually filter out, high frequency components, for example signals above 100 Hz and in some case even lower thresholds such as 75 Hz or even 50 Hz. In general the noise level is such that high frequency components cannot be reliably isolated from a single ECG trace. In order to obtain high frequency components one typically needs to align ECG traces from successive heartbeats so that noise cancels.

One feature that appears from the high frequency component following alignment is the reduced amplitude zone or RAZ. The presence or absence of RAZ is discussed in the following patent disclosures:

U.S. Pat. No. 7,113,820 filed Jul. 12, 2001 and U.S. Pat. No. 7,539,535 filed Jan. 26, 2006 both disclose real time cardiac electrical data being received from a patient, manipulated to determine various useful aspects of the ECG signal, and displayed in real time in a useful form on a computer screen or monitor. The monitor displays the high to frequency data from the QRS complex in units of microvolts, juxtaposed with a display of conventional ECG data in units of millivolts or microvolts. The high frequency data are analyzed for their root mean square (RMS) voltage values and the discrete RMS values and related parameters are displayed in real time. The high frequency data from the QRS complex are analyzed with imbedded algorithms to determine the presence or absence of reduced amplitude zones, referred to herein as "RAZs". RAZs are displayed as "go, no-go" signals on the computer monitor. The RMS and related values of the high frequency components are displayed as time varying signals, and the presence or absence of RAZs may be similarly displayed over time.

In U.S. Pat. No. 7,386,340 filed Mar. 26, 2003, a system for the diagnosis and monitoring of coronary artery disease, acute coronary syndromes, cardiomyopathy and other cardiac conditions is disclosed. Cardiac electrical data are received from a patient, manipulated to determine various useful aspects of the ECG signal, and displayed and stored in a useful form using a computer. The computer monitor displays various useful information, and in particular graphically displays various permutations of reduced amplitude zones and kurtosis that increase the rapidity and accuracy of cardiac diagnoses. The disclosure provides criteria for recognizing reduced amplitude zones that enhance the sensitivity and specificity for detecting cardiac abnormalities.

The above disclosures have in common that they decide whether or not a RAZ is present and draw their conclusions from that.

SUMMARY OF THE INVENTION

Although several studies have shown the correlation of RAZ and myocardial ischemia, there is currently no way of quantifying the RAZ and using such quantity in order to detect a heart condition such as for example, acute coronary syndrome (ACS) or infer the seriousness of a condition or changes in the condition. The present embodiments introduce an apparatus and method for quantifying the RAZ and thereby allowing early detection of ACS with an indication of seriousness and also permitting a means of monitoring for changes in the condition.

The present embodiments provide an index of the RAZ, which index can be to obtained from a patient at various times to diagnose some acute cardiac event as well as to indicate the initial state of the patient undergoing a suspected cardiac event and the patient's subsequent response to intervention. Typically, under these circumstances a resting ECG is used.

According to an aspect of some embodiments of the present invention there is provided ECG apparatus comprising:

an ECG input for obtaining wideband ECG signals;
a high frequency analyzer configured for:
obtaining high frequency QRS components from a QRS complex within the ECG signals and a low frequency envelope around the high frequency QRS components, and
identifying within the envelope at least one reduced amplitude zone—RAZ—present within a given QRS complex; and
a RAZ quantifier configured for obtaining a quantification of the at least one RAZ region within the QRS complex.

In an embodiment, the quantification is used to compute an index that is proportional to an area of the RAZ within the QRS complex.

In an embodiment, the index comprises a ratio between an area of the at least one RAZ and an area within the envelope.

In an embodiment, the area of the at least one RAZ is an area over a local minimum in the envelope between two flanking maxima in the envelope.

In an embodiment, the area of at least one RAZ is measured by connecting respective flanking maxima.

In an embodiment, the area of at least one RAZ is measured under a horizontal line at a height of one of the flanking maxima, or by connecting peaks of the flanking maxima or by estimating an expected peak without RAZ by extrapolation and calculating a difference in areas.

In an embodiment, the high frequency analyzer is configured to obtain the high frequency components by aligning QRS complexes of successive heartbeats to cancel noise.

An embodiment may comprise a plurality of leads, the apparatus configured to obtain a quantification of the RAZ for each lead respectively and to calculate an to overall RAZ quantification statistically from the respective lead quantifications.

In an embodiment, the plurality of leads comprises 12 leads and the statistical calculation comprises taking an average of one or more highest lead quantifications.

An embodiment may comprise an output module configured to indicate myocardial ischemia in the presence of a relatively high RAZ quantification.

In an embodiment, the output module is further configured to use a falling RAZ quantification over time to indicate successful interventions.

An embodiment may be included at least partly within an implantable device.

According to a second aspect of the present invention there is provided an ECG method comprising:

obtaining ECG signals;
obtaining high frequency QRS components from a QRS complex within the ECG signals,
obtaining a low frequency envelope around the high frequency components,
identifying therein at least one reduced amplitude zone—RAZ—present within a given QRS complex; and
obtaining a quantification of the at least one RAZ region within the QRS complex.

Embodiments may involve indicating myocardial ischemia in the presence of a relatively high RAZ quantification, or using a falling RAZ quantification over time to indicate successful interventions.

Embodiments may involve obtaining a first quantification relatively soon after onset of a suspected myocardial infarction and obtaining subsequent quantifications at succeeding time points thereafter.

Embodiments may involve providing quality analysis by measuring the quantification successively over a moving time window to determine stability.

Embodiments may involve indicating myocardial ischemia during a monitoring period on the basis of changes in the RAZ quantification over time.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. The data processor may include a volatile memory for storing instructions and/or data and/or a non-volatile storage, for example, a magnetic hard-disk, flash memory and/or removable media, for storing instructions and/or data. A network connection may be provided and a display and/or a user input device such as a keyboard or mouse may be available as necessary.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a simplified block diagram schematically illustrating the main blocks of an ECG device according to embodiments of the present invention;

FIG. 2 is a schematic diagram illustrating the positioning of electrodes for a 12 lead ECG, according to known art;

FIG. 3 is a schematic flow chart illustrating a procedure for processing a high resolution ECG to provide a RAZ quantification according to an embodiment of the present invention;

FIGS. 4A to 4E are simplified diagrams showing envelopes drawn around high frequency components of the QRS complex and illustrating various ways of quantifying the RAZ area;

FIG. 5 is a graph showing the RAZ envelope and changes therein according to the present embodiments as a patient enters hospital with a complaint and then undergoes treatment;

FIG. 6 is a simplified graph illustrating HFMI according to embodiments of the present invention for different groups of patients at admission, post angio and after 24 hours; and FIG. 7 is a simplified set of ECG readings and RAZ envelope diagrams according to the present embodiments taken for a patient determined not to have an acute cardiac condition.

DESCRIPTION OF SPECIFIC EMBODIMENTS OF THE INVENTION

Figure 1:
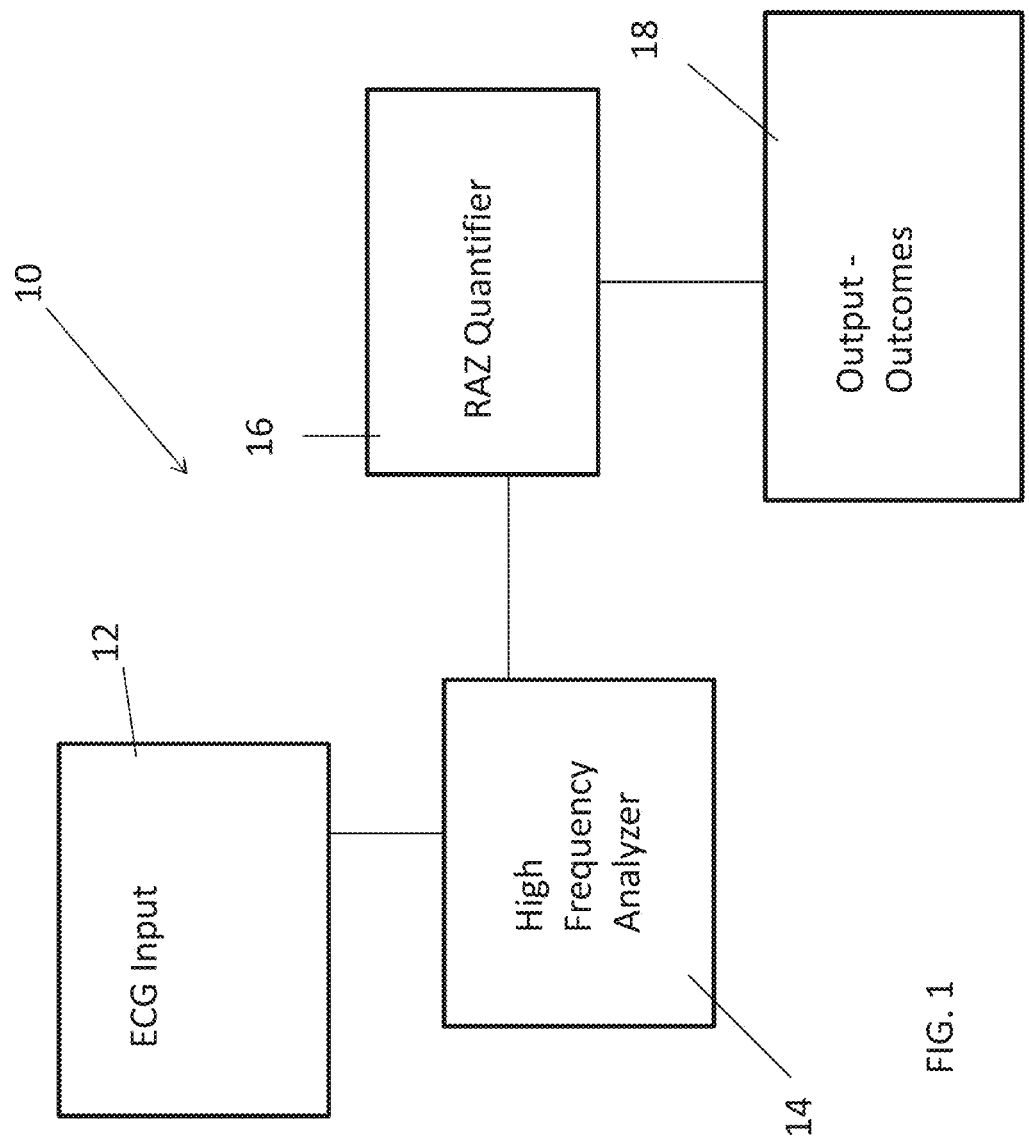

The present invention, in some embodiments thereof, relates to quantification of the RAZ and use of that quantification to draw conclusions about the state of a patient's heart.

Embodiments provide an electrocardiograph with a wide bandwidth capability able to record and analyze high frequency signals with high resolution. The QRS to complexes are detected in all the leads and throughout the entire duration of the test. The high frequency components of the QRS (HFQRS) are filtered to be further analyzed. If the signal to noise ratio (SNR) of the HFQRS is not sufficient for reliable analysis, as is many times the case, several wideband or unfiltered QRS complexes from the same lead are aligned and subsequently averaged to increase the SNR. The averaged signal is then filtered to obtain the HFQRS.

A low frequency envelope is computed for the HFQRS, and Reduced Amplitude Zones (RAZ) in this envelope are sought. Such RAZ can be depicted as basins and one or more may exist in the HFQRS envelope. The area of the basins is computed and the ratio of that area to the area under the envelope is defined to be a new index. This new index is named the High Frequency Morphology Index (HFMI) and may be used for detecting acute coronary syndrome as a RAZ in fact is believed to arise from changes in the electrophysiological properties of certain parts of the myocardium, changes which may be attributed to myocardial ischemia.

The present embodiments may thus be useful as a signal processing element in the diagnostic process of patients presenting with chest pain, who today are monitored or treated in various ways, all of which suffer from relatively low sensitivity and/or specificity. By measuring the HFMI in real time, the clinical team at a hospital, emergency room, ambulance or other clinical settings, may have an additional valuable indication of possible acute ischemia. As a direct consequence, better care may be offered to cardiac patients, who can benefit from an earlier and more accurate diagnosis and treatment, as well as to non-cardiac patients, who may avoid false-positive diagnosis and unnecessary further procedures.

The present embodiments provide various alternate ways of computing the HFMI. The signal processing pathway for filtering the HFQRS affects the obtained envelope and therefore the basins. The methods of computing the envelope from the filtered HFQRS signal also affect the area of the basins. In addition, the exact method of defining the basin's area along with the way in which multiple basins are treated, both have a direct effect on the HFMI. All of these methods, which are detailed below, are independent and thus can be applied independently and then may be combined for enhanced efficiency.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a simplified block diagram showing an ECG apparatus 10 according to embodiments of the present invention. An ECG input 12 obtains ECG signals from one or more ECG leads, typically between 3 and 12. FIG. 2 illustrates a typical layout for a 12 lead ECG.

A high frequency analyzer 14 obtains high frequency QRS components from the QRS complexes within the ECG signals from the various leads. Within the high frequency components one or more reduced amplitude zones—RAZ—may be identified within any given QRS complex, as will be explained in greater detail below.

A RAZ quantifier 16 obtains a quantification of the RAZ within the QRS complex. As will be explained in greater detail below, if there are several RAZ regions then the quantification may use all of the regions, or an average, or the largest region or any other reasonable configuration. As long as the quantification is consistent any configuration of the different RAZ regions may work, and the skilled person will be able to select between the different methods to obtain the clearest result.

An output module 18 uses the quantification of the RAZ to estimate myocardial ischemia. In the presence of a relatively high RAZ quantification, myocardial ischemia is inferred. A falling RAZ quantification over time is taken as a sign of successful interventions or a natural healing process (spontaneous reperfusion).

Reference is now made to FIG. 3, which is a simplified flow chart showing the quantification process of FIG. 1. In stage A, alignment and averaging of successive QRS complexes of a high resolution resting ECG is carried out. Aligning QRS complexes of successive heartbeats reinforces the signal and cancels noise.

In stage B the averaged ECG is filtered and in stage C a high frequency QRS signal is obtained. An envelope is then drawn around the high frequency QRS signal in stage D and a basin area is obtained between two adjacent peaks of the envelope, based on the water hole principle as discussed hereinbelow. The basin area, shown in hashing, is the RAZ area, and a ratio between the RAZ area and the area within the envelope is calculated for each lead. Then, an average or other statistical derivation may be calculated over all the leads in stage E.

The envelope is typically a low frequency envelope, and may be obtained using a Hilbert transform, as discussed in greater detail below. The hashed area shown in FIG. 3 stage D provides the basin, and the quantification may be defined as a ratio between the area of the RAZ basin and an area within the envelope. Alternatively, as discussed below, the absolute area of the RAZ could be used. If there is more than one basin then, as will be explained in greater detail below, the area of the largest basin may be used, or alternatively a sum of a given number of largest basins or a sum of all the basins may be used.

Figure 4A:
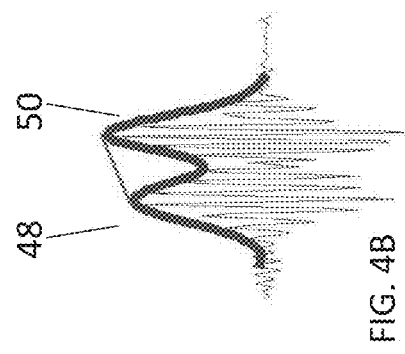

The area of the RAZ, the hashed area of FIG. 3 stage D may be defined as an area over a local minimum in the RAZ in question between two flanking maxima. Such an area is indicated as 40 in FIG. 4A, where 42 and 44 denote the flanking maxima and 46 denotes the local minimum. The hashed area mentioned above may for example be measured by taking the upper or lower of the two maxima and connecting it via a horizontal line to the upsloping segment of the other maxima. An example of such a line drawn from an upper maxima is shown in FIG. 4C and one from a lower maxima is depicted in FIG. 3D.

Figure 4B:
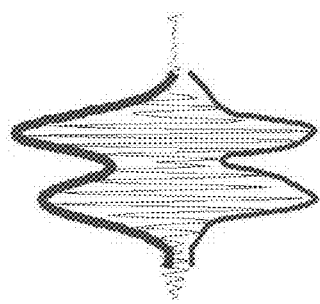

As shown in FIG. 4B the area may also be measured by connecting peaks 48 and 50 of respective flanking maxima.

Figure 4C:
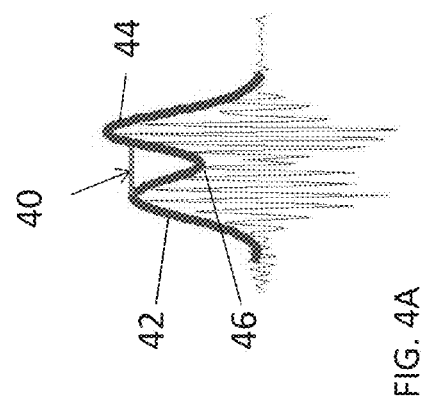

In FIG. 4C, another alternative is shown in which the area is measured under a horizontal line at a height of one of the flanking maxima, 52 and 54. As shown the higher of the two maxima is used, but the lower could alternatively be used, as shown in FIG. 3D.

In an embodiment, the apparatus may be included partly or wholly within an implantable device, say for long term monitoring of highly at risk patients. The device uses implantable electrodes that can be intracardiac or epicardiac electrodes. A device according to the present embodiments may be useful in detection of ischemia, and provides measurement of the ECG signal between two implantable electrodes, or between an implantable electrode and the can of the implantable device, and identifies changes in RAZ area.

In a preferred embodiment of the invention a high resolution wideband ECG acquisition device is used for sampling the ECG signal at a rate of 1000 Hz. The analog to digital converter employs high resolution so that signal changes of at least 1 microvolt can be reliably received and recorded.

The analysis algorithm as discussed above with reference to FIG. 3, uses a template-based correlation to identify valid QRS complexes and exclude noisy or ectopic beats. Careful beat alignment, followed by beat averaging, is used to increase the signal-to-noise ratio. The level of noise in the HFQRS signal may be calculated as the root-mean-square of high frequency components within the ST segment. Beat averaging is applied to each of the leads until the level of noise is for example ≥1 µV. Other thresholds may be used and averaging within a fixed window is an option. Beats with low signal to noise ratio are removed from further processing. Each valid average QRS complex is filtered by a band-pass filter in the frequency band of 140 Hz to 250 Hz, although similar frequency bands, wider, narrower or somewhat shifted, may also be used. The filtered signal, which includes the high frequency components of the QRS complex is defined as the HFQRS. The time-domain envelope of the HFQRS complex is calculated using a Hilbert transform followed by a low pass filter. In this envelope, RAZ are quantified by computing the ratio of the area of the basins to the area under the envelope, as explained. An index, referred to hereinbelow as HFMI, is calculated for each average HFQRS complex, and the median index of all valid complexes in a lead is determined to be the HFMI value of the lead. As alternatives to the median, points with minimal noise or may be selected, or any other suitable method may be used. HFMI value per patient may be defined as the average of a number of leads which may be chosen to be those with maximal index value, or via any other suitable statistical measure.

In order to reliably compute the HFMI, the filtered HFQRS signal requires a high signal to noise ratio. Since the recorded ECG signal is usually tainted by noise from various sources, in most practical scenarios the SNR may be improved by signal to processing methods. These include standard procedures such as filtering outside noise sources, like the mains power frequency (50 Hz/60 Hz) but also collecting multiple QRS complexes from the same lead and averaging them to obtain a higher SNR as discussed above. The averaging process includes detecting the QRS complexes in the ECG signal, defining a template for a QRS complex and subsequently correlating each QRS complex with the template to decide whether or not this specific complex should be included in the averaging process. The selected complexes are then aligned, possibly using sub-sampling accuracy and averaged to obtain the wideband QRS complex which includes the entire sampled bandwidth of the signal, where the HFQRS is usually negligible compared to the low frequency QRS signal amplitude. The alignment process may be carried out using a partial bandwidth, e.g. a mid-range frequency band such as 30 Hz-70 Hz. Filtering out the lower frequencies for the alignment process results in more accurate alignment, but since most of the signal's energy is found in the lower frequencies, SNR considerations inhibit the use of higher frequency ranges—hence the choice of the mid range frequency band.

Averaging multiple QRS complexes increases the SNR, but may distort the signal, for example if the HFQRS changes during the averaged time span. Thus it is helpful to keep the averaged segment at a minimum and an optimal averaging duration is sought. Such an averaging duration can be arbitrarily determined but it can also be adaptive by specifying the required noise level or SNR. Defining the noise level can be difficult since multiple sources of noise exist. One of the possibilities is measuring the high frequency ECG signal at a certain part of the cycle, where no high frequency signal is expected so that any signal measured in such a part of the cycle may be considered as noise. Such a process can be carried out using the root mean square signal of the ST segment. It is assumed that the high frequency noise level in the QRS complex is identical to that of the ST segment. The averaging can thus be determined to include the minimal number of sequential template-correlated QRS complexes whose matching signal level in the ST segment is lower than the noise threshold, for example, under 1 microvolt.

Since the HFMI is computed from minute high frequency components, with respect to the much higher-voltage low frequency components, it is provided that the analog to digital converter (ADC) which samples the signal has a high resolution. However, due to the averaging process described above, the requirements for the ADC may be relaxed. Even if microvolt levels of the signal are to be analyzed, lower resolution ADC's may be employed since the averaged signal will have a better resolution and accuracy than the original sampled signal, a phenomenon known as super resolution.

While QRS complexes from different leads cannot be averaged, they may still be aligned. Thus, various parameters such as detecting the QRS, defining its central location in the time domain and its time domain boundaries may be computed considering more than a single lead. All of the ECG leads signals may be synchronized so that every time point in one lead may be directly matched with a similar time point in a different lead. By taking advantage of this synchronization, a more accurate estimate of the QRS parameters mentioned above may be achieved compared with similar estimates based on a single lead.

The HFQRS has a typical shape such as the one depicted in FIG. 3C. It has been previously shown that Reduced Amplitude Zones (RAZ) are indicative of changes in myocardium conduction, which may be caused by myocardial ischemia. The high frequency components in the QRS are attributed to the fractal nature of the electric activation signal dispersing in the myocardium. This pattern is brought about by the numerous purkinje fibers which stimulate multiple groups of myocytes to contract. As a result of ischemia the myocyte to myocyte conduction is impaired and thus there are fewer discrete sources of effective signals that propagate through the tissue, leading to a more uniform and smooth propagation front and consequently to less high frequency content during depolarization. The RAZ is a result of the tissue inhomogeneity which translates to temporal differences in the ECG signal. Thus signals arriving from ischemic tissue will have a lower component of high frequencies than signals which emanate from healthy tissue. The depiction of these temporal differences in the amount of high frequency components is what is shown in the reduced amplitude zones. To detect RAZ one may study the envelope of the HFQRS, but the envelope is not a clearly defined attribute, nor is it straightforward to compute. The present embodiments use any of several methods in order to obtain the envelope such as full wave or half wave rectification, using the Hilbert transform or other digital processing techniques. Various low pass filters may be used in order to smooth to the envelope.

Regardless of the method used for detecting the envelope, RAZ in the envelope is defined and the corresponding area is computed. One way is to look at the RAZ as if it is a basin filled with water as depicted in FIG. 3D. The area so to speak filled with water corresponds to the area of the RAZ. In one method the area is delimited by the lowest peak of the two peaks delimiting the RAZ. Another method for computing the area is taking a straight line between these two peaks as demonstrated in FIG. 4B. Yet another method considers the highest peak and takes a horizontal line between it and a vertical line from the lower peak, as depicted in FIG. 4C. Generally speaking, the area of the RAZ may be computed as a function of the distance between sequential local minima and maxima of the envelope and the amplitude differences between them. In its most crude form this area may be a rectangle, but other more elaborate schemes, such as these described above may be used.

Figure 4D:
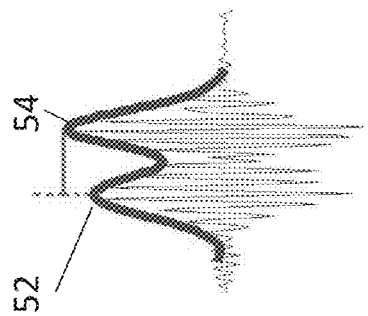
Figure 4E:
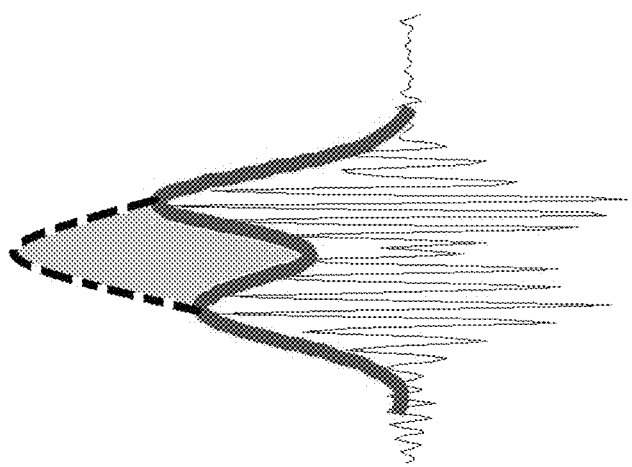

FIG. 4E illustrates a further option for quantifying RAZ. An estimate is made by extrapolation of an expected peak without RAZ. The difference in areas, shown shaded, is then calculated. As discussed above, the envelope of the QRS complex may be low pass filtered.

When multiple RAZ exist, the area may be defined in several ways. It may be the sum of all the areas, regardless of how they were computed. It may also be the largest area, i.e. ignoring small RAZ.

Since the HFQRS includes, by definition, only high frequency components, the signal has no DC component and some of the signal values will be positive while others will be negative and the signal in general will be centered around zero. In a similar manner to the detection of the positive envelope discussed so far, a negative envelope may be detected for the lower part of the HFQRS where the signal has negative values. Not all of the methods described above are suitable for this task. For example, full wave rectification is insensitive to the sign, but half wave rectification will yield generally different results for the positive and negative envelopes, as shown in FIG. 4D. The negative envelope may be used in two ways. First, it may be used in a similar manner to the positive envelope with all of the methods described above. Second, it may be used in conjunction with the positive envelope yielding roughly to double the area since both the upper and lower (upside down) basins are additionally considered.

The area of the basins described above is a parameter to consider when analyzing the HFQRS. The area is affected by some circumstances such as the signal amplitude. In order to consider a more robust index of the HFQRS morphology, we turn to the High Frequency Morphology Index, HFMI, referred to above, which also considers the area under the HFQRS envelope. The HFMI is the ratio of both areas, i.e. the area of the basins divided by the area under the envelope. In the case of a negative envelope or a double sided envelope, the area in the denominator may be the area above the envelope or between the envelopes respectively.

The above has discussed various methods of computing the HFMI. The procedure may be carried out for all of the available leads and for any duration of test, although very short tests may not have sufficient data to allow acceptable SNR. When considering the time span of the ECG signal used for extracting a single measurement of HFMI for a specific lead, it is apparent that any number of HFMI values may be obtained for every lead, when the ECG test is long enough. The HFMI value may therefore be studied as a function of time, say when used in monitoring the progress of a patient. The diagnosis may be based on changes in the HFMI over time. The idea is that the one measurement of HFMI may not be sufficiently high to require attention, but if the patient is monitored for a long time, this somewhat high value (but not high enough to pass the threshold) may be indicative of ischemia, when considering the duration of the high HFMI value, its slope and similar factors.

Another possibility is to seek a single result for assessing a patient's condition at a particular point in time. Any number of statistical tools may be used to determine the HFMI value from the set of values obtained for each lead. These include: median, mean, maxima, minima etc.

When used for monitoring, the quality of the test may be assessed by using a moving window. Each window may be treated as a measurement and the variation of the measurement over time, e.g. the standard deviation, may indicate the degree of the test quality where a stable result in a stationary situation may indicate high quality measurements.

In a study at the intensive coronary care unit (ICCU) of Soroka Medical Center, the following results were obtained using the embodiment described above:

Out of 32 patients who met the criteria for study inclusion and had a complete set of three ECG recordings, HFQRS analysis was available in 30 patients (age 55±11 yrs, 26 men). The remaining 2 patients presented inadequate signal quality and were excluded from the analysis. Most patients (97%) did not have previously diagnosed coronary artery disease (CAD). Fifteen patients (50%) had 3 or more coronary risk factors.

The majority of patients (26 pts, 87%) had ST-elevation MI (STEMI). Of these patients, 17 were urgently reperfused, with a door-to-balloon time of 87±23 minutes. In 8 STEMI patients spontaneous reperfusion occurred prior to angiography, ensuing resolution of their ST segment changes by the time of admission. One patient had a recent STEMI. In all patients except one, angiography indicated significant coronary artery disease CAD (≥70% stenosis in a major coronary artery, or ≥50% stenosis in the left-main artery). Successful revascularization by angioplasty was achieved in 24 pts (80%). Of the patients with no revascularization, four were referred for coronary artery bypass graft CABG, one had failed percutaneous coronary intervention PCI and one had insignificant CAD. These patients were included in the analysis, although their serial ECG recordings were acquired before intervention. The TIMI risk score for STEMI 18, calculated for 26 STEMI patients, was 2.2±1.8 (Mean±SD). The average time between onset of symptoms and acquisition of 1st high-resolution ECG at the ICCU was 5.8±6 hours. Post-revascularization ECG was acquired 0.7±0.8 hrs after angiography, and 24 h ECG was acquired 26.1±15 hrs following angiography.

The ECG at ICCU admission was interpreted by the blind observer as 'ischemic' in 19 pts (63%), 'non-ischemic' in 9 pts (30%) and 'inconclusive' in 2 pts (7%). ECG was non-ischemic in 6 STEMI patients with spontaneous reperfusion and 2 NSTEMI patients. After 24 hours, 32% of the patients with ischemic admission ECG had non-ischemic or inconclusive ECG, and 45% of the patients with non-ischemic or inconclusive admission ECG had indications of ischemia or infarction.

Figure 5:
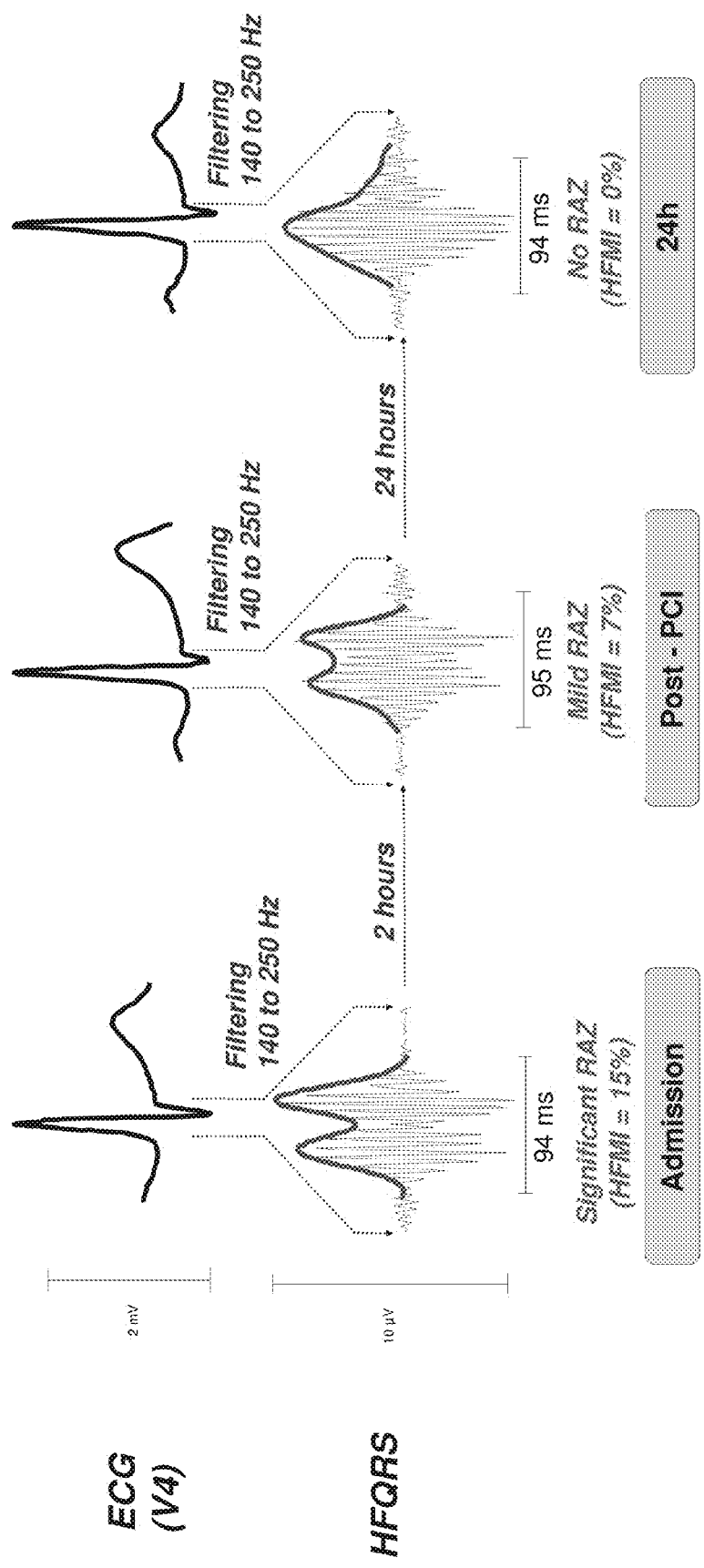

A typical example of HFQRS analysis results is given in FIG. 5, for a 41 yr old male patient with STEMI. The patient, without history of CAD, was diagnosed with acute anterior STEMI in the emergency department before being admitted to the ICCU. Admission ECG, acquired 2.25 hours after onset of symptoms, showed spontaneous ST resolution, although chest pain persisted. HFQRS exhibited significant ischemic morphology (RAZ pattern) in multiple leads, with HEMI=15% in a typical lead (V4). Urgent angiography, performed 2 hours after admission, revealed two-vessel disease with total occlusion of the mid-LAD and critical occlusion of a first marginal branch. Both vessels were successfully dilated. Post-revascularization ECG was normal, and HFQRS signal exhibited partial resolution of RAZ morphology, with HFMI=7%. At 24 h, both conventional ECG and HFQRS morphology did not indicate ongoing ischemia.

Figure 6:
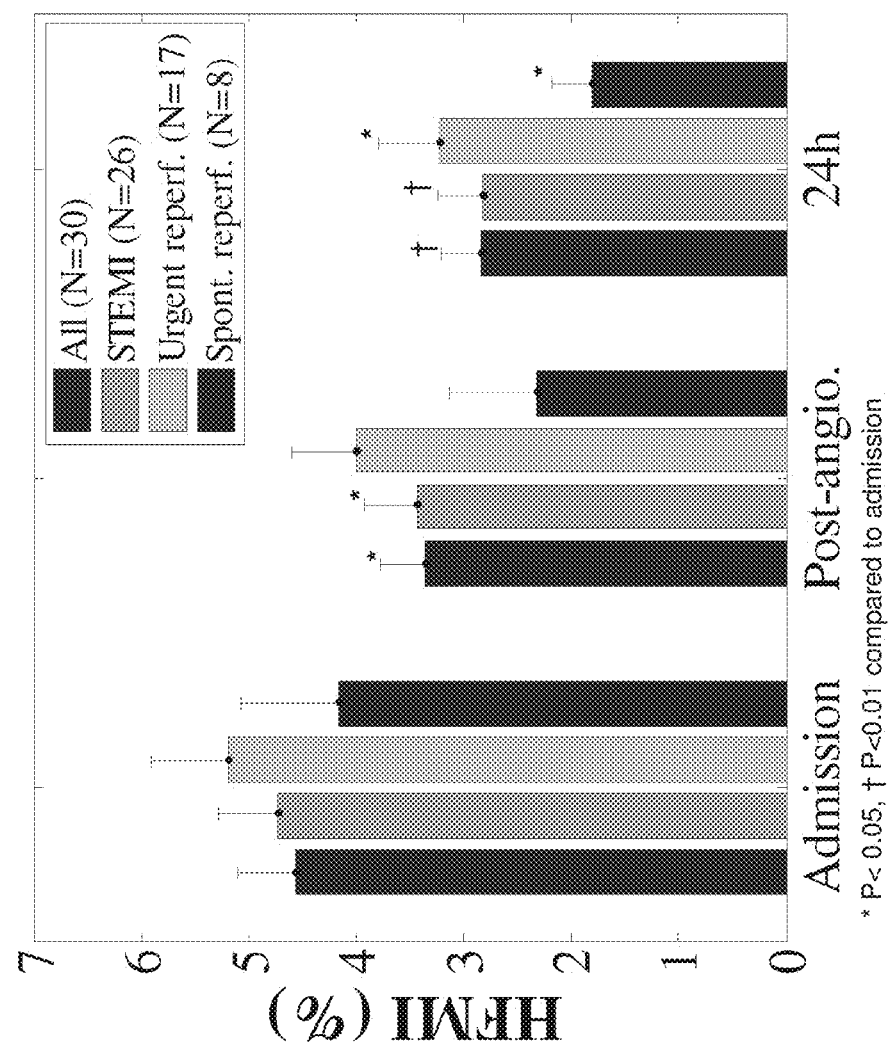

The values of HFMI per patient were higher on the admission ECG than on the post-angiography ECG (4.6±2.9% vs. 3.4±2.3%, P<0.05) and the 24 h ECG (4.6±2.9% vs. 2.8±2.1%, P<0.01), as shown in FIG. 6, which is a graph showing HFMI at three different times for different groupings of the patients. The number of leads with HFMI value >3%, was higher on the admission ECG, compared to post-angiography ECG (3.4±2.7 vs. 2.1±2, P<0.03) and 24 h ECG (3.4±2.7 vs. 2.1±1.8, P<0.02). The trend of decrease in average HFMI values, following angiography and after 24 h was also observed in subgroups of STEMI patients who were referred for urgent reperfusion, as well as in patients with spontaneous reperfusion. Compared to patients who underwent urgent reperfusion, in those with spontaneous reperfusion HFMI values tended to be lower during admission, post-angiography and 24 h. This difference was not statistically significant, possibly due to the small sample size.

HFMI value decreased from admission ECG to 24 h ECG in 71% of the patients in the analysis group, and in 79% of the patients who were revascularized by angioplasty.

Figure 7:
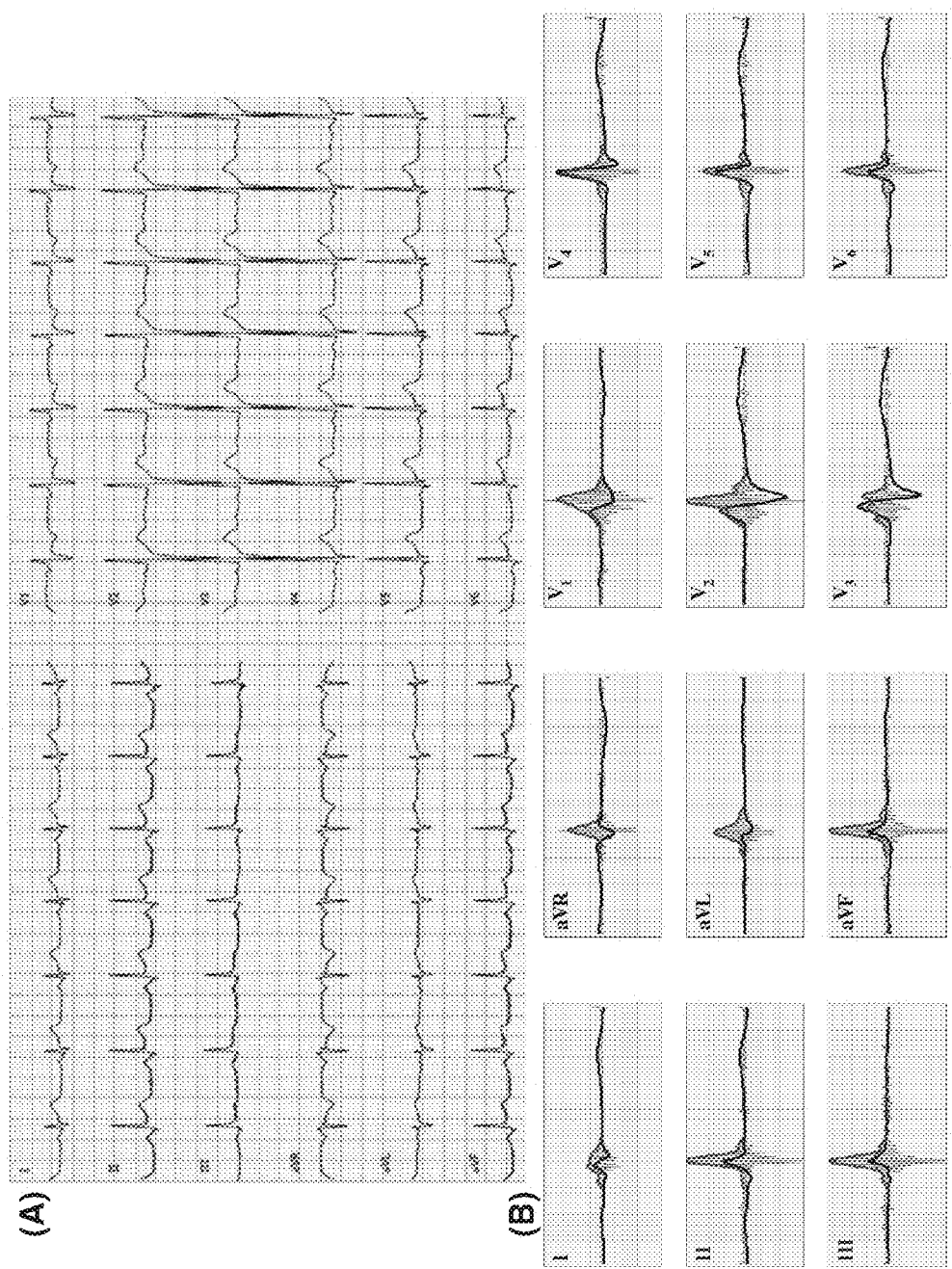

A noteworthy case of a patient excluded from the analysis group is shown in FIG. 7. The patient, a 30 yr-old male with no risk factors was admitted due to acute chest pain and elevated Troponin-T (0.8 ng/mL), following 5 days of viral common cold disease. Admission ECG showed diffuse ST segment elevations (FIG. 7A) and the patient was referred for urgent angiography, which demonstrated normal coronary arteries. HFQRS analysis revealed normal signal morphology, with apparent RAZ in to only one of the leads as shown in FIG. 7B. The discharge diagnosis was perimyocarditis, and no adverse cardiac events were documented during a 7-month follow-up period.

It is expected that during the life of a patent maturing from this application many relevant pulse shaping and symbol decoding technologies will be developed and the scope of the corresponding terms in the present description are intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be to construed as necessarily limiting.

What is claimed is:

1. ECG apparatus comprising:
an ECG input for obtaining wideband ECG signals;
a high frequency analyzer configured for:
obtaining high frequency QRS components from a QRS complex within said ECG signals and a low frequency envelope around said high frequency QRS components, and
identifying within said envelope at least one reduced amplitude zone—RAZ—present within a given QRS complex; and
a RAZ quantifier configured for obtaining a quantification of said at least one RAZ region within said QRS complex, wherein said quantification is used to compute an index that is proportional to an area of said RAZ within said QRS complex.

2. The ECG apparatus of claim 1, wherein said index comprises a ratio between an area of the at least one RAZ and an area within the envelope.

3. The ECG apparatus of claim 2, wherein said area of the at least one RAZ is an area over a local minimum in said envelope between two flanking maxima in said envelope.

4. The ECG apparatus of claim 3, wherein said area of at least one RAZ is measured by connecting respective flanking maxima.

5. The ECG apparatus of claim 3, wherein said area of at least one RAZ is measured under a horizontal line at a height of one of said flanking maxima, or by connecting peaks of said flanking maxima or by estimating an expected peak without RAZ by extrapolation and calculating a difference in areas.

6. The ECG apparatus of claim 1, wherein said high frequency analyzer is configured to obtain said high frequency components by aligning QRS complexes of successive heartbeats to cancel noise.

7. The ECG apparatus of claim 1, comprising a plurality of leads, the apparatus configured to obtain a quantification of said RAZ for each lead respectively and to calculate an overall RAZ quantification statistically from said respective lead quantifications.

8. The ECG apparatus of claim 7, wherein said plurality of leads comprises 12 leads and said statistical calculation comprises taking an average of one or more highest lead quantifications.

9. The apparatus of claim 1 further comprising an output module configured to indicate myocardial ischemia in the presence of a relatively high RAZ quantification.

10. The apparatus of claim 9, wherein said output module is further configured to use a falling RAZ quantification over time to indicate successful interventions.

11. The apparatus of claim 1, included at least partly within an implantable device.

12. ECG method comprising:
obtaining ECG signals;
obtaining high frequency QRS components from a QRS complex within said ECG signals,
obtaining a low frequency envelope around said high frequency components,
identifying therein at least one reduced amplitude zone—RAZ—present within a given QRS complex; and
obtaining a quantification of said at least one RAZ region within said QRS complex, wherein said quantification is proportional to a size of said RAZ within said QRS complex.

13. ECG method comprising:
obtaining ECG signals;
obtaining high frequency QRS components from a QRS complex within said ECG signals,
obtaining a low frequency envelope around said high frequency components,
identifying therein at least one reduced amplitude zone—RAZ—present within a given QRS complex; and
obtaining a quantification of said at least one RAZ region within said QRS complex, wherein said obtaining a quantification comprising obtaining a ratio between an area of the at least one RAZ and an area within the envelope.

14. ECG method comprising:
obtaining ECG signals;
obtaining high frequency QRS components from a QRS complex within said ECG signals,
obtaining a low frequency envelope around said high frequency components,
identifying therein at least one reduced amplitude zone—RAZ—present within a given QRS complex; and
obtaining a quantification of said at least one RAZ region within said QRS complex, wherein said area of the at least one RAZ is an area over a local minimum in said envelope between two flanking maxima of said envelope, or wherein said area of at least one RAZ is measured by connecting said respective flanking maxima, or wherein said area of at least one RAZ is measured under a horizontal line at a height of one of said flanking maxima, or wherein said area of at least one RAZ is measured by connecting peaks of said flanking maxima, or wherein said area of at least one RAZ is measured by estimating an expected peak without RAZ by extrapolation and calculating a difference in areas.

15. The ECG method of claim 12, comprising obtaining said high frequency components by aligning QRS complexes of successive heartbeats to cancel noise.

16. The ECG method of claim 12, comprising using a plurality of ECG leads, the method comprising obtaining a quantification of said RAZ for each lead respectively and calculating an overall RAZ quantification statistically from said respective lead quantifications.

17. The method of claim 12, further comprising indicating myocardial ischemia in the presence of a relatively high RAZ quantification.

18. The method of claim 17, further comprising using a falling RAZ quantification over time to indicate successful interventions.

19. The method of claim 12, comprising obtaining a first quantification relatively soon after onset of a suspected myocardial infarction and obtaining subsequent quantifications at succeeding time points thereafter.

20. The method of claim 12, further comprising providing quality analysis by measuring said quantification successively over a moving time window to determine stability.

21. The method of claim 12, comprising indicating myocardial ischemia during a monitoring period on the basis of changes in said RAZ quantification over time.

* * * * *